United States Patent
Rendon Montoya et al.

(10) Patent No.: US 10,546,097 B2
(45) Date of Patent: Jan. 28, 2020

(54) ANALYZER SYSTEM OF SOUND GENERATED IN MILLS BASED ON EMBEDDED SYSTEMS AND A MICROPHONE ARRAY

(71) Applicant: ELECTRO CONTROLES DEL NOROESTE S.A. DE C.V., Sonora (MX)

(72) Inventors: Alvaro Rendon Montoya, Sonora (MX); Luis German Ruiz Maytorena, Sonora (MX); Guzman Gerardo Alfonso Sanchez Schmitz, Sonora (MX); Oscar Samuel Cortez Moreno, Sonora (MX)

(73) Assignee: ELECTRO CONTROLES DEL NOROSESTE S.A. DE C.V., Hermosillo (MX)

( * ) Notice: Subject to any disclaimer, the term of this patent is extended or adjusted under 35 U.S.C. 154(b) by 282 days.

(21) Appl. No.: 15/537,311

(22) PCT Filed: Dec. 17, 2015

(86) PCT No.: PCT/MX2015/000213
§ 371 (c)(1),
(2) Date: Jun. 16, 2017

(87) PCT Pub. No.: WO2016/099242
PCT Pub. Date: Jun. 23, 2016

(65) Prior Publication Data
US 2018/0045684 A1 Feb. 15, 2018

(30) Foreign Application Priority Data
Dec. 18, 2014 (MX) .................. MX/a/2014/015828

(51) Int. Cl.
*G06F 19/00* (2018.01)
*G01N 29/04* (2006.01)
(Continued)

(52) U.S. Cl.
CPC .............. *G06F 19/00* (2013.01); *B02C 17/18* (2013.01); *G01H 3/00* (2013.01); *G01H 3/08* (2013.01);
(Continued)

(58) Field of Classification Search
CPC ...... B02C 17/18; B02C 2210/01; G01H 3/00; G01H 3/08; H04R 2201/401; H04R 23/006; H04R 3/005; G06F 19/00
See application file for complete search history.

(56) References Cited

U.S. PATENT DOCUMENTS

| 4,722,485 A * | 2/1988 | Young | B02C 25/00 241/179 |
| 6,510,729 B2 * | 1/2003 | Bonnevie | G01N 17/02 204/404 |

(Continued)

FOREIGN PATENT DOCUMENTS

| CA | 2456608 | 7/2004 |
| ES | 8704759 A1 | 7/1987 |

*Primary Examiner* — Francis C Gray
(74) *Attorney, Agent, or Firm* — Thorpe North & Western, LLP

(57) ABSTRACT

This invention consists of a new analyzer system of the sounds generated in mills that capture the signals issued by the mineral and steel balls cascade that perform grinding. These signals are processed in an embedded system (2) formed by a field programmable gates array (FPGA) and a processor. The system is comprised of an industrial microphone array (1) that captures the sound signals that are converted from analog to digital through and acquisition system (3) specialized in sound signals, processed by a FPGA capable of performing parallel operations at high (Continued)

speed due to the customized hardware developed for this application, and sent to the processor through a high-speed data bus.

6 Claims, 2 Drawing Sheets

(51) Int. Cl.
  *B02C 17/18* (2006.01)
  *G01H 3/00* (2006.01)
  *G01N 29/46* (2006.01)
  *G01N 29/24* (2006.01)
  *G01N 29/14* (2006.01)
  *G01H 3/08* (2006.01)
  *H04R 23/00* (2006.01)
  *H04R 3/00* (2006.01)

(52) U.S. Cl.
  CPC .............. *G01N 29/04* (2013.01); *G01N 29/14* (2013.01); *G01N 29/2475* (2013.01); *G01N 29/46* (2013.01); *H04R 23/006* (2013.01); *B02C 2210/01* (2013.01); *G01N 2291/106* (2013.01); *H04R 3/005* (2013.01); *H04R 2201/401* (2013.01)

(56) References Cited

U.S. PATENT DOCUMENTS

| | | | |
|---|---|---|---|
| 6,874,364 B1* | 4/2005 | Campbell | B02C 17/1805 73/593 |
| 9,321,054 B2* | 4/2016 | Held | B02C 17/1805 |
| 9,789,515 B2* | 10/2017 | Hajati | B06B 1/0622 |
| 9,974,466 B2* | 5/2018 | Kimmel | A61B 5/1114 |
| 2004/0255679 A1* | 12/2004 | Valderrama Reyes | G01H 1/003 73/649 |
| 2004/0255680 A1* | 12/2004 | Ortega | B02C 17/1805 73/649 |
| 2006/0288787 A1* | 12/2006 | Mistry | G01B 7/282 73/660 |
| 2009/0248194 A1* | 10/2009 | Lammering | G05B 19/4163 700/173 |
| 2014/0150524 A1 | 6/2014 | Magne et al. | |
| 2018/0126384 A1* | 5/2018 | Robles Opazo | B02C 17/1805 |

\* cited by examiner

ANALYZER SYSTEM OF SOUND GENERATED IN MILLS BASED ON EMBEDDED SYSTEMS AND A MICROPHONE ARRAY

INVENTION FIELD

This invention, mentioned in the title of this descriptive report, falls within the fields of mining and control systems, particularly to an analyzer system of sound generated by mills that operate within the mining field and specific to an embedded system of sound analysis that allows measurement and estimation of fundamental parameters regarding the internal operation of a mill for the optimization of the grinding process.

SUBJECT MATTER OF THE INVENTION

The first noteworthy item regarding this invention concerns a new analyzer system of sound generated in mills based on embedded systems and a microphone array in order to optimize the addition of the load, the steel balls, and the water in the grinding circuit, as well as to optimize the life of the balls and the mill's inner lining, with a direct impact in energy consumption savings. The system is compact, being comprised of a microphone that captures sound signals from the cascade of mineral and steel balls, which carry out the grinding, and it sends the signals to an embedded system for their analysis in real-time.

BACKGROUND OF THE INVENTION

Generally, the sound generated by the mills is the parameter used to estimate the proper operation of the mills, since it is a highly complex process to implement.

Over the years, different instruments and computer systems have been commonly used for sound analysis in a wide variety of processes such as cement production, plastic bottle fabrication, food conservation, and mineral processing. The latter field still reveals deficiencies despite the current existence of products for monitoring the condition of this equipment, thus culminating in large fields of study and development that could potentially increase process efficiency.

Specifically, grinding is a technique used to grind metals or non-metallic minerals, a process that is present in mining plants. The grinding process allows for the reduction of the size of the mineral up to having the final desired size through several items that work through impact, crushing or wear. There are several types of mills, such as ball mills, bar mills, FAG (autogenous) mills and SAG (semi-autogenous) mills. Most of the mills operate under the same principle, which consists of elevating the material within a cylindrical mill up to the point that they fall again to the bottom of the mill. The elevation of the load (mineral to grind, balls to carry out the grinding, and water) is performed by the rotation of the mill, making use of equipment that transports the material called 1the inner lining. The combined action of impacts, falls, slippage, and crushing of the ore reduce the size of the particles as they advance through the mill.

Currently, there are grinding systems that have certain disadvantages that limit efficiency. The inside of mills have a short life span due to the level of impact it receives, which lends itself to the mill being used less frequently as a result of stoppages in production and for repairs and increases the cost of the mineral grinding line. Thus, some systems have been developed to obtain information from the mill.

Due to the difficulties in instrumenting a mill so as to understand its internal operation, the sound emitted becomes a key parameter. Currently, the device called "Electric Ear" is one of the most used instruments. This device estimates the volume of the mill occupied by the mineral, grinding means, and/or water, comprised of a microphone that detects the intensity of the noise close to the mill, without distinguishing whether the origin of the noise was caused by the movement of the mill or by an external cause independent of the grinding process. It has an exit electrical signal for the control system. Only the operator is in charge of keeping a proper noise level, since the instrument does not carry out any other analysis that provides information about the internal operation of the mill.

The sound analysis system currently used in mills, captures and analyzes sound signals in real-time by a centralized system, which also processes sound and communicates with the control system by means of the OPC (Object Linking and Embedding for Process Control).

Currently, systems use servers with special hardware features designed to execute advanced analysis algorithms; these require large memory space, high speed, etc. The system communicates with databases to save and analyze data and transfer it to the control systems.

The following patents serve as a background. This is the case of the descriptive report for the Spanish Patent with Publication No. ES8704759 and priority number ZA19850003617 19850514, which describes a procedure and device to monitor the load level in the mills, which include: a) detecting the prevailing sound level in two positions, b) generating signals that depend on the sound level of two positions, c) comparing the sound levels signals, and d) generating a control signal to regulate the load feeding regime to the mill. It consists of the following: two sound level detectors of the impact located between both detectors, a signal gauge of the detectors that generates a control signal, a visual representation that indicates the point of impact, and a control module that increases the mineral feeding regime.

In the descriptive report of the United States Patent with Publication Number US20040255679 and priority number 190-2003 31.01.2003 CL, an instrument that uses four to eight sound detectors, unites with industrial data acquisition and a processing system based on computers where virtual instrumentation software is executed. The types of impact that occurred are detected and classified, a record is created, and mill operation risk is determined. This is shown to the operator on a display, through graphs of each microphone.

The descriptive report of the Canadian Patent with Publication Number CA2456608 and priority number 189-203 31.01.2003 CL is very similar, where a system and method of direct, dynamic, and online measurement of different parameters are described, which are related to the volume occupied by the internal dynamic load of tube mills when the mill is in operation. More specifically, an online measurement of the total filling of volumetric dynamic load, volumetric dynamic of the balls load, and the apparent density of the mill internal load are undertaken. This includes a series of wireless acoustic sensors connected to the external body of the mill, a receptor and/or conditioning units located close to the mill, a processing unit, and a communication unit.

Despite the advancement and sophistication that these technologies represent, there are some associated disadvantages. First, current systems used to analyze the sound in the mills are instruments that process the signals in an analog manner, using components such as operation amplifiers, thus a deep analysis of the signal is not performed, yet the system is imitated in order to make comparisons of intensity.

In turn, current systems are, in reality, a software solution, thus the performance in terms of response time and reliability are not optimal. Second, these require diverse components to function such as servers, storage, cameras, and data communication that collectively deliver results to the control system. Using servers and diverse components make these systems more costly and difficult to use; additionally, they require more maintenance. Both the software and hardware of a server are generally determinant elements; specific software and hardware is necessary to meet application needs. In a server, if the numbers of users at any given time were high, the server would stop responding to the users thus, without being able to know that the system failed, communication with the control would be incorrect.

Industrial quality OPCs demand complex configuration procedures, making them not feasible for plant personnel; therefore, to use OPCs, hours of engineering and maintenance from qualified personnel are required in order to establish a proper and efficient use in the design and administration of databases. The implementation can be costly, regarding both the physical equipment (servers, memory, installations, etc.) and the logical equipment (operating systems, software, etc.). In addition to the database acquisition and maintenance cost, the equipment requires a high volume hard disk and sufficient RAM capacity to work properly. In the event that the database becomes corrupted, the recovery process is much more complex to implement. The fact that everything is centralized makes the system more vulnerable to potential failure, thus it is necessary to make security copies regularly The system requires high bandwidth since it transfers images to the server in order to analyze them while not interrupting data flow at the information level.

Finally, the systems that perform the sound processing techniques are computer systems with software for image analysis at the information network level; that is to say, there is no direct communication with the control system in addition to not being deterministic systems.

Therefore, an area of opportunity related to current technologies consists of a system that analyses the sound and reduces the complexity and cost of current equipment, without affecting the efficiency and precision required to carry out the analysis which in turn can be compact and robust equipment. For example, an embedded vision system that works at the controller level may be used, this way the use of servers and components that make the system costly and complex would not be required, allowing the facility to be part of a control system such as a remote node controlled by a master controller.

DETAILED DESCRIPTION OF THE INVENTION

Figure 1:
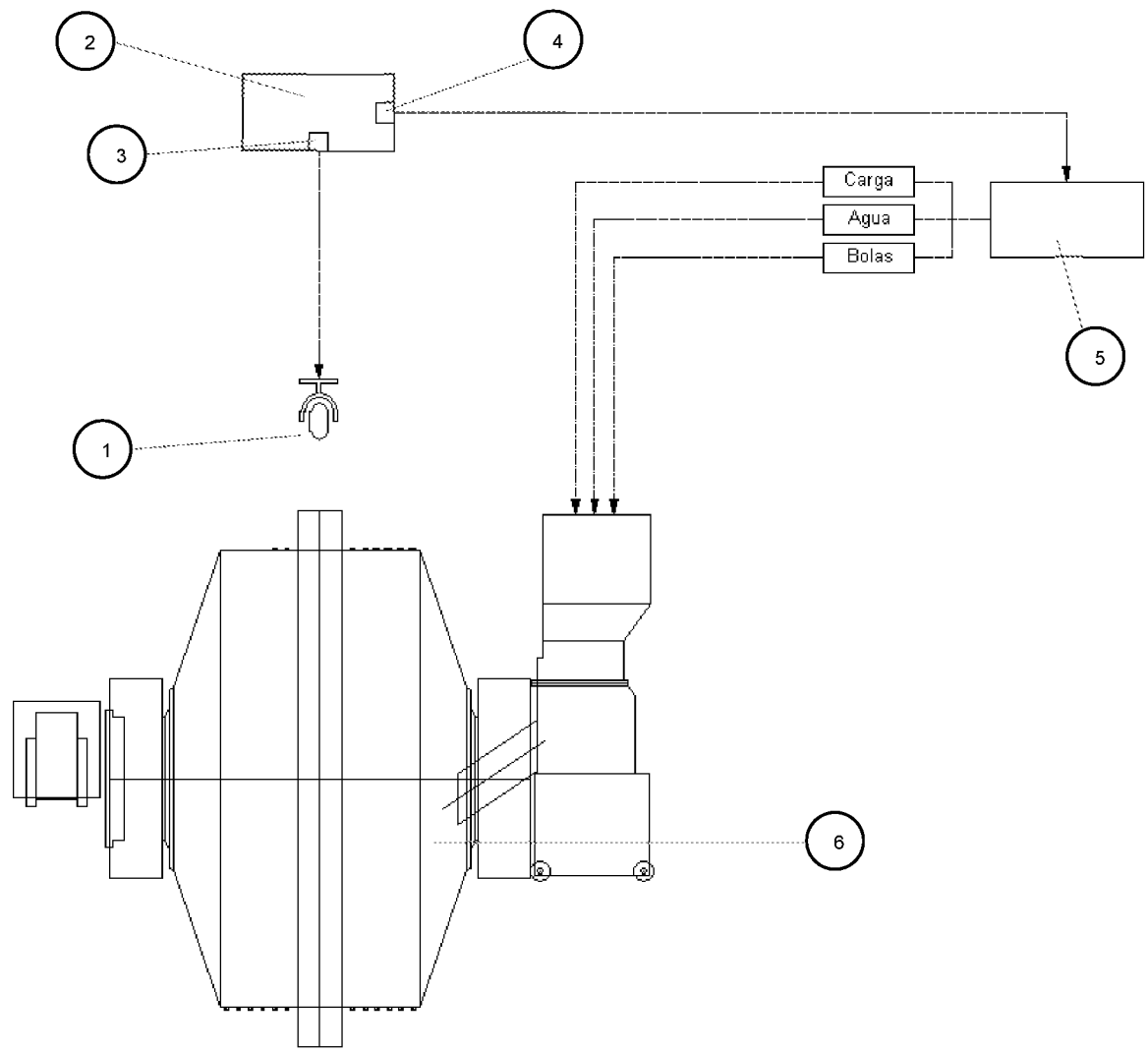
FIG. 1. Operating mode followed by the analyzer system of the sound generated in mills based on embedded systems and a microphone array.
Figure 2:
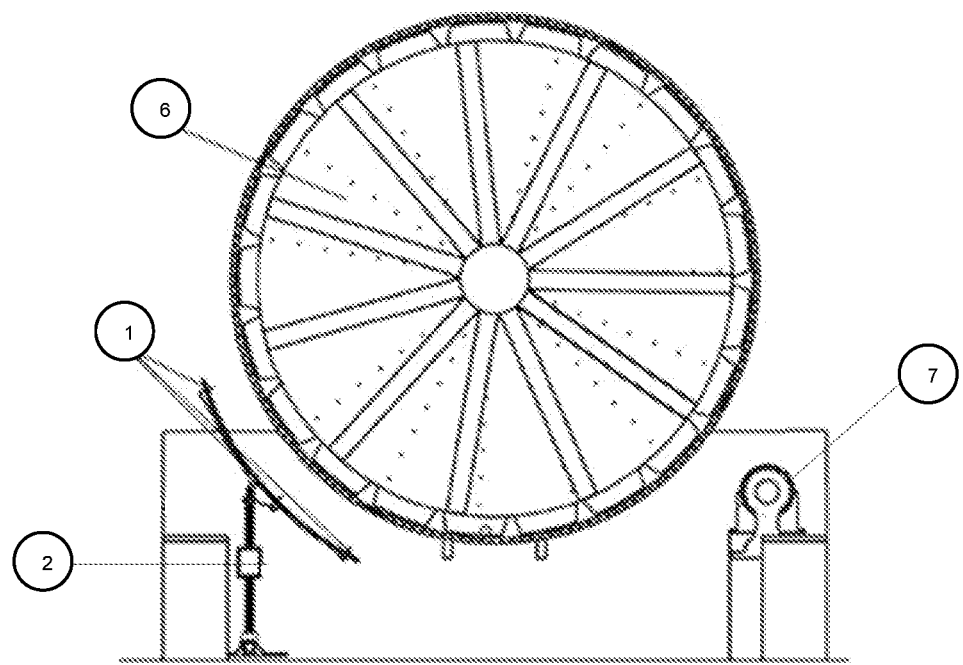
FIG. 2.—Representative view of the structure that supports the microphones and the noise analyzer system in a SAG mill.
Figure 3:
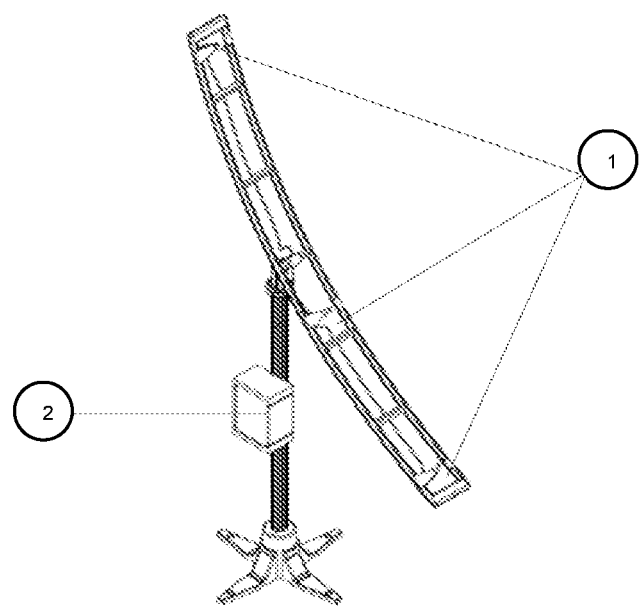
FIG. 3.—Representative view of the structure that supports the microphones and the noise analyzer system in a SAG mill.

As mentioned in the title of this descriptive report, the invention refers to an Analyzer System of Sound Generated in Mills Based on Embedded Systems and a Microphone Array. The characteristic details of this product are clearly shown in the following description and in the accompanying figures.

The system is able to carry out analysis in the time and frequency domain, obtaining parameters such as sound power in different bands of frequency and time lapses, as well as estimate the fall angle of cascading materials. The results of the analysis are sent via communication with industrial protocol toward the mill control systems, collaborating with the optimization of the additions of load, steel balls and water. It is possible to estimate the wear of the inner lining and steel balls, preventing risk conditions that can cause undesired stoppages in work during the process. The benefits of the invention directly impact the mill's energy consumption, the efficient use of steel balls, and the lifespan of the inner lining.

The invention features a new system that analyzes the sound generated in mills based on embedded systems and a microphone array, in order to estimate their operation, wear, and function during the optimized control of the mineral grinding process. This system applies mainly to semi-autogenous mills (SAG) (6) and ball mills, where mineral and steel ball cascading takes place, these being the components that carry out the grinding process.

The system is composed of an array of industrial microphones (1) that capture sound signals at a distance close to the mill housing (6), placing a microphone (1) in the central point where the cascade of material theoretically tends to fall and where most amount of impact occurs, in contrast to the mill motor (7). Two additional microphones are placed equidistantly to the first microphone, forming an array of three microphones (1) that enables the cascade falling angle to be obtained. The microphones (1) used have industrial features such as maximum signal amplification facing the sound source (directional), wide frequency range and linearity.

The embedded system (2) includes the specialized signal acquirer (3), a processor and a FPGA. Signals are converted from analog to digital through the acquisition system (3) specialized in sound signals such as filtering, high sampling speed and large dynamic range, which allows for obtaining a high quality signal without information loss. These signals are processed by the FPGA, which is capable of performing operations in parallel at high speed due to the development of hardware customized for this application, allowing signal filtering and transformation to the frequency domain of all of the sound signals simultaneously. The signals are sent from the FPGA to the processor via a high-speed data bus. The processor features multicore architecture and possesses a real-time operating system. Here, the algorithms of digital analysis of signals and statistics function to determine the sound power, frequency bands, estimation of the cascade angles through measurement of each microphone and averaging the relevant pick in every signal. The processor has the function of carrying out the communication with the EtherNet/IP industrial protocol, allowing for communication with a remote node that enables a data exchange with the mill controller.

When the system is worked at controller level through a second Ethernet/IP interface (4), it is able to send the results to an external control system (5) that used the results of the invention described here to execute control actions. Additionally, the interface (4) can be used to manipulate the application and the set up of the parameters through a GUI.

The system conducts a frequency analysis that allows it to relate the power level of the frequency band spectrum with the type of impact that occurs in the mill, such as the impact sounds between balls and mineral and those of balls and inner linings. These spectra are variable according to mill conditions; thus the frequency bands to be analyzed are user-configurable.

The methodology to determine the cascade angle of minerals and balls is determined by the sound level detected in the microphones; estimating the angle according to the microphone placed where higher sound levels are detected.

The system takes samples of the signals for analysis determined by a complete mill revolution. To achieve this, the system uses an inductive sensor that sends it a signal each time the mill performs a turn; alternatively, it is possible to obtain this information from the revolutions per minute performed by the mill that are sent from the control system through industrial communication. This allows for taking samples of the sound signals in each section of the mill, integrating all the parts of the signals per section in only one signal in order to, at a later stage, average the sound level. This provides an estimation of the wear of the inner linings, since worn linings emit a more powerful sound.

The hardware components of the sound analyzer system are:

A real-time processing system (2) that includes:

A processor for signal analysis and communication with industrial protocol that features multicore architecture.

An FPGA module for signal processing and adaptation.

Acquisition system (3) of high quality sound signals.

Industrial microphones (1) for collection of sound signals.

Ethernet/IP industrial communication module.

One of the main advantages is that it works directly in the control network through its interconnection with the control system as a remote node using Ethernet/IP communication that sends the analysis results in order for the control system to execute the actions necessary to optimize grinding. Another advantage is that it can work simultaneously with the information network, sending to the monitoring computer the analysis results. It demonstrates the advantage of being a deterministic system, carrying out the processing in an uninterrupted rate of time thus adding to the reliability of the execution of algorithms and communication. The system resets in parallel with the control system, reestablishing the communication immediately.

Preferred Embodiment of the Invention

SAG mills (6) use 3 industrial microphones (1), an embedded system (2) comprised of: an acquisition system (3) of high quality sound signals, an FPGA for processing and adaptation of signals, a processor for signal and communication analysis and a PLC connection via industrial communication; Additionally, it features robust protection for electronic components and a metallic structure for placing the microphones.

The system will acquire the following parameters: total sound level, estimated point and angle where the material and grinding balls cascade impact, detection of critical impact, and estimation of wear of the lining and balls.

Ball mills use the same components that are used for SAG mills (6). The parameters that are obtained in the ball mills are: total sound level, distribution of the load along the mill, and estimation of wear of the internal components (lining and grinding balls).

Process for SAG Mills:

The 3 microphones (1) are placed in points where the material cascade can fall, while placing the central microphone at the optimal point where the cascade should fall.

The microphones (1) are connected to the acquisition system (3) of the embedded system (2), which digitalizes the signal with industrial quality.

Digital signals enter the FPGA device. This device sets up the signal acquisition module (3) and executes processing signal algorithms such as the spectrum analysis. Moreover, this device dynamically communicates with the processor through special buses.

The processor performs signal analysis functions and determines the parameters. Besides this, it is responsible for communicating with the PLC using industrial protocols.

The information is received by a control system, which includes, as claimed, dedicated instruction for the invention; here is where process optimization occurs together with the other instruments.

Process for Ball Mills:

The 3 or more microphones are placed along the mill.

Digital signals enter the FPGA device. This device sets up the acquisition module and executes processing signal algorithms such as the spectrum analysis. Moreover, this device dynamically communicates with the processor through special buses.

The processor performs signal analysis functions and determines the parameters. Besides this, it is responsible for communicating with the PLC using industrial protocols.

The information is received by a control system, which, as claimed, includes dedicated instruction for the invention; here is where the process optimization occurs together with the other instruments.

We claim:

1. Analyzer system of sound generated in mills based on embedded systems and a microphone array, the system comprising:

an industrial microphone array positioned near a mill housing that acquires sound signals from said mill;

an embedded system that receives the sound signals acquired from the industrial microphone array, wherein the embedded system comprises a signal acquirer, a processor and a FPGA type chip;

the signal acquirer in communication with the industrial microphone array wherein the signal acquirer converts analog sound signals from the industrial microphone array to digital sound signals;

a multicore processor with a real-time operative system that sends results via an Ethernet TCP/IP communication protocol, wherein the processor includes;

an FPGA type chip that sends the sound signals to the multicore processor and simultaneously performs signal filtering and signal transformation;

wherein the system collects samples of the signals to analyze, determined by a complete revolution of the mill based on the value of revolutions per minute that the controller sends, or through an inductive sensor that sends a signal each time that the mill performs a turn, wherein each sound signal made by a complete turn is separated in time sections related to the time in which the inner lining crossed by the microphone and wherein the signal parts are later integrated into only one signal to carry out a new frequency spectrum analysis at a later period, thus determining the wear per inner lining according to the sound levels detected.

2. The analyzer system according to claim 1, wherein for ball mills the system determines the distribution of minerals and balls along the mill through sound levels that are detected in the microphone array, which are placed along the mill.

3. The analyzer system according to claim 1, wherein for SAG mills the following parameters can be found: total sound level, estimated point and angle where the material and grinding balls cascade impact, detection of critical impacts, and estimation of lining and balls wear.

4. The analyzer system according to claim 1, wherein for ball mills the following parameters can be found: total sound level, distribution of the load along the mill and estimation of wear of the inner components (lining and grinding balls).

5. The analyzer system according to claim 1, wherein a first microphone from the industrial microphone array features a maximum signal amplification facing the sound source, wide frequency range and linearity.

6. The analyzer system according to claim 5, wherein two additional microphones are placed equidistantly to said first microphone forming an array of three microphones.

* * * * *